(12) United States Patent
Brienza et al.

(10) Patent No.: US 10,376,412 B2
(45) Date of Patent: Aug. 13, 2019

(54) ACTIVELY AND SELECTIVELY COOLED CUSHIONING SURFACE

(71) Applicants: David M. Brienza, Allison Park, PA (US); Patricia E. Karg, South Park, PA (US); Andrew J. Malkiewicz, Pittsburgh, PA (US)

(72) Inventors: David M. Brienza, Allison Park, PA (US); Patricia E. Karg, South Park, PA (US); Andrew J. Malkiewicz, Pittsburgh, PA (US)

(73) Assignee: University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 1404 days.

(21) Appl. No.: 13/943,772

(22) Filed: Jul. 16, 2013

(65) Prior Publication Data
US 2014/0228918 A1    Aug. 14, 2014

Related U.S. Application Data

(60) Provisional application No. 61/672,202, filed on Jul. 16, 2012.

(51) Int. Cl.
*A61F 7/00* (2006.01)
*A61F 7/02* (2006.01)
*A61F 7/10* (2006.01)

(52) U.S. Cl.
CPC ........ *A61F 7/10* (2013.01); *A61F 2007/0056* (2013.01); *A61F 2007/0076* (2013.01); *A61F 2007/0219* (2013.01); *A61F 2007/0268* (2013.01)

(58) Field of Classification Search
CPC ........ A61F 2007/029; A61F 2007/0054–0056; A61F 2007/0075; A61F 2007/0076; A61F 2007/0219; A61F 2007/0268; A61F 2007/0273
See application file for complete search history.

(56) References Cited

U.S. PATENT DOCUMENTS

| 2,648,325 | A | * | 8/1953 | Siple | A41D 13/0051 |
| | | | | | 126/204 |
| 3,136,577 | A | * | 6/1964 | Richard | B60N 2/5692 |
| | | | | | 219/202 |
| 4,846,176 | A | * | 7/1989 | Golden | A61F 7/02 |
| | | | | | 165/46 |
| 4,854,319 | A | * | 8/1989 | Tobin | A61F 7/10 |
| | | | | | 2/171.2 |
| 4,962,761 | A | * | 10/1990 | Golden | A61F 7/02 |
| | | | | | 165/46 |

(Continued)

*Primary Examiner* — Kaitlyn E Smith
(74) *Attorney, Agent, or Firm* — Paul D. Bangor, Jr.; Clark Hill PLC

(57) ABSTRACT

A cushioning surface for cooling tissue that reaches a predefined level of immersion into the cushioning surface, comprising: a segmented fluid cushion comprising a plurality of cells interconnected to allow fluid to flow from each cell to at least one of the other plurality of cells; and wherein one or more of the plurality of cells contains a heat exchange material. The cushioning surface may further comprise a cooling element associated with and for removing heat from the one or more cells containing a heat exchange material.

12 Claims, 8 Drawing Sheets

Thermoelectrically cooled air cell under load

(56) References Cited

U.S. PATENT DOCUMENTS

| | | | | |
|---|---|---|---|---|
| 5,010,608 | A * | 4/1991 | Barnett | A61G 7/05776 5/713 |
| 5,456,703 | A * | 10/1995 | Beeuwkes, III | A61F 7/02 607/109 |
| 5,533,217 | A * | 7/1996 | Holdredge | A61G 5/1043 5/710 |
| 5,840,080 | A * | 11/1998 | Der Ovanesian | A61F 7/02 607/112 |
| 5,957,964 | A * | 9/1999 | Ceravolo | A61F 7/10 607/109 |
| 5,989,285 | A * | 11/1999 | DeVilbiss et al. | A47C 21/044 607/104 |
| 6,235,049 | B1 * | 5/2001 | Nazerian | A61F 7/007 607/108 |
| 6,800,088 | B1 * | 10/2004 | Karapetyan | A61F 7/103 607/104 |
| 6,927,316 | B1 * | 8/2005 | Faries, Jr. | A41D 13/1245 602/14 |
| 7,744,640 | B1 * | 6/2010 | Faries, Jr. | A61F 13/00 607/108 |
| 9,433,525 | B2 * | 9/2016 | Parish | A61F 7/0097 |
| 2005/0256556 | A1 * | 11/2005 | Schirrmacher | A61F 7/02 607/104 |
| 2006/0060344 | A1 * | 3/2006 | Esaki | B60H 1/00285 165/287 |
| 2007/0135878 | A1 * | 6/2007 | Lachenbruch | A61G 7/057 607/108 |
| 2007/0150033 | A1 * | 6/2007 | Johnson | A61F 7/106 607/114 |
| 2008/0077202 | A1 * | 3/2008 | Levinson | A61F 7/02 607/96 |
| 2008/0287839 | A1 * | 11/2008 | Rosen | A61F 7/10 601/18 |
| 2009/0033130 | A1 * | 2/2009 | Marquette | A47C 7/74 297/180.15 |
| 2009/0198311 | A1 * | 8/2009 | Johnson | A61F 7/106 607/109 |
| 2009/0287281 | A1 * | 11/2009 | Munson | A61F 7/02 607/104 |
| 2010/0274332 | A1 * | 10/2010 | Hirakawa | A47C 21/042 607/114 |
| 2011/0307040 | A1 * | 12/2011 | Peterson | A61F 7/02 607/108 |
| 2012/0065715 | A1 * | 3/2012 | Carson | A61F 7/10 607/104 |
| 2012/0305231 | A1 * | 12/2012 | Liang | A61F 7/0241 165/287 |
| 2013/0067662 | A1 * | 3/2013 | Jusiak | B32B 3/26 5/724 |
| 2013/0079684 | A1 * | 3/2013 | Rosen | A61F 7/10 601/11 |
| 2013/0116760 | A1 * | 5/2013 | Carson | A61F 7/10 607/104 |
| 2013/0269106 | A1 * | 10/2013 | Brykalski | A47C 21/048 5/423 |
| 2014/0214138 | A1 * | 7/2014 | Voorhees | A61F 7/10 607/104 |
| 2015/0107601 | A1 * | 4/2015 | Arnone | A61F 7/03 128/845 |
| 2016/0128487 | A1 * | 5/2016 | Eskridge, III | A47C 21/048 5/423 |

* cited by examiner

Individual cooling elements situated inside air chambers
A gel pad sits atop a thermoelectric cooler and the
chamber is resealed using neoprene epoxy Thermoelectrically cooled air cell under load Labview control program GUI Control thermistor test locations. (A) Within Gel. (B) Above Gel.
(C) Below gel in contact with TEC. (D) On skin of seated user

ACTIVELY AND SELECTIVELY COOLED CUSHIONING SURFACE

RELATED APPLICATIONS

This application claims priority benefit under 35 U.S.C. § 119(e) of U.S. Provisional Patent Application No. 61/672,202, filed Jul. 16, 2012, the contents of which are herein incorporated by reference.

GOVERNMENTAL RIGHTS

This invention was made with government support under Grant #H133E070024 awarded by the United States Dept of Education, National Institute on Disability and Rehabilitation Research (Federal-non-NIH). The government has certain rights in the invention.

TECHNICAL FIELD

The present disclosure generally relates to cushioning surfaces for use in wheelchair seating/support applications and other applications including, without limitation, beds, mattresses, mattress overlays, operating table pads, face masks, helmets and shoe insoles and, more specifically, to cushioning surfaces having areas that may be actively and selectively cooled depending upon the application and particularly where a cushioned body part or tissue reaches a predefined level of immersion into the cushioning surface.

BACKGROUND

Pressure ulcers result from excessive pressure applied to fragile tissue over an extended period of time. The wounds usually occur over bony prominences where weight bearing soft tissue is compressed. The most common anatomical locations are the sacrum, heels and ischial tuberocities. Known risk factors include pressure, shear force, heat, moisture, aging skin, immobility, lack of sensation, poor nutrition, diabetes and a host of other conditions. The cause is believed to be ischemia, ischemia-reperfusion injury, or simply mechanical damage due to cell deformation. Populations at high risk include the immobile elderly, persons with paralysis and/or neurological deficits, and people undergoing long surgical procedures. Primary prevention involves frequent repositioning and the provision of a cushioning surface that redistributes pressure away from vulnerable areas.

Fifteen years ago, a group of researchers at the University of Minnesota (Kokate et al., 1995) demonstrated the critical importance of skin temperature to the susceptibility of tissue to ulceration when the tissue is exposed to ischemia inducing compressive forces. In an experiment on the backs of swine, pressure (100 mmHg) was selectively applied with skin temperature controlled at 25° C., 35° C., 40° C. and 45° C. for five hour periods. Histological examination at 7 days post-procedure showed that all tissue layers were normal under 25° C., while moderate muscle damage was found at sites with 35° C., and tissue necrosis at all layers was found at sites with 45° C. In a follow up study, Iaizzo (1995) narrowed the temperature range to 25° C., 27° C., 30° C. and 32° C. in an attempt to find a critical temperature. The results were not conclusive, but based on the relationship between temperature and damage severity that they observed, they suggested temperatures below 30° C. had a protective effect for the conditions of the experiment. The fundamental effect of the cooling is believed to be a lowering of the metabolic rate (consumption of $O_2$) in ischemic tissue allowing the cells to survive for a longer period of time without oxygen.

Despite Kokate and Iaizzo's demonstration of the prophylactic effect of maintaining skin temperature at levels below core body temperature and below typical skin temperature, no cushions, mattresses, operating table overlays, or other cushioning surfaces have been brought to market that actively cool the skin in an attempt to prevent pressure ulcers. Possible explanations for this are numerous, but chief among them is the undesirable effect of lowering core body temperature in an attempt to cool the skin impacted by weight bearing. A potential solution is to limit the location where cooling is applied to only those locations where pressure exceeds a given threshold, thus limiting the overall effect on the body while cooling the most critical areas. Iaizzo and others, e.g., Augustine, et al., U.S. Pat. No. 6,497,720, teach the concept of applying active cooling in response to pressure. Such pressure sensitive cooling techniques for cushioning are complex. A simpler approach according to preferred embodiments of the present disclosure comprises an actively and selectively cooled cushioning surface with embedded cooling mechanisms that cool tissue that reaches a predefined level of immersion into the cushioning surface (i.e., immersion-based cooling).

SUMMARY

One aspect of a preferred embodiment of the present disclosure comprises a cushioning surface for cooling tissue that reaches a predefined level of immersion into the cushioning surface, comprising: a segmented fluid cushion comprising a plurality of cells interconnected to allow fluid to flow from each cell to at least one of the other plurality of cells; and wherein one or more of the plurality of cells contains a heat exchange material. The cushioning surface may preferably further comprise a cooling element associated with and for removing heat from the one or more cells containing a heat exchange material.

In another aspect of a preferred embodiment of the present disclosure, the cushioning surface preferably comprises top and bottom surfaces and the heat exchange material is disposed between the top surface and the cooling element.

In an additional aspect of a preferred embodiment of the present disclosure, the cushioning surface preferably further comprises a separate cooling element associated with each of the one or more cells containing heat exchange material for removing heat from the heat exchange material in each such cell.

In another aspect of a preferred embodiment of the present disclosure, the cushioning surface preferably comprises top and bottom surfaces and the heat exchange material is disposed between the top surface and the separate cooling element in each of the one or more cells containing heat exchange material.

In yet another aspect of a preferred embodiment of the present disclosure, the cushioning surface may preferably comprise a plurality of air-filled cells.

In another aspect of a preferred embodiment of the present disclosure, the cushioning surface may preferably comprise a cooling element comprising a powered thermoelectric cooler.

In a further aspect of a preferred embodiment of the present disclosure, the cushioning surface may preferably comprise a heat exchange material comprising a compliant material or gel.

In another aspect of a preferred embodiment of the present disclosure, the cushioning surface may preferably comprise a plurality of cells each containing heat exchange material and having a separate cooling element associated therewith.

In an additional aspect of a preferred embodiment of the present disclosure, the cushioning surface may preferably one or more cells each containing heat exchange material and having a separate cooling element associated therewith and corresponding to an area where immersion of tissue into the cushioning surface at the predefined level is expected to occur from a body supported by the cushioning surface or from a person seated on the cushioning surface.

Another aspect of a preferred embodiment of the present disclosure comprises a cushioning surface for cooling tissue that reaches a predefined level of immersion into the cushioning surface, comprising: a segmented fluid cushion comprising a plurality of cells interconnected to allow fluid to flow from each cell to at least one other of the plurality of cells; wherein a plurality of the plurality of cells contains a heat exchange material; a separate cooling element associated with each of the cells containing heat exchange material for removing heat therefrom; and wherein the cushioning surface comprises top and bottom surfaces and the heat exchange material is disposed between the top surface and the separate cooling element in each of the cells containing heat exchange material.

In an additional aspect of the cushioning surface a preferred embodiment of the present disclosure, each cell containing heat exchange material and having a separate cooling element associated therewith corresponds to an area where immersion of tissue into the cushioning surface at the predefined level is expected to occur from a body supported by the cushioning surface or from a person seated on the cushioning surface.

Another aspect of a preferred embodiment of the present disclosure comprises a cushioning surface for cooling tissue that reaches a deep level of immersion into the cushioning surface, comprising: a segmented air cushion comprising a plurality of cells interconnected to allow air to flow from each cell to at least one other of the plurality of cells; wherein at least one of the plurality of cells contains a heat exchange material; a separate cooling element associated with the at least one cell containing heat exchange material for removing heat therefrom; wherein the cushioning surface comprises top and bottom surfaces and the heat exchange material is disposed between the top surface and the separate cooling element in each of the at least one cell containing heat exchange material; and wherein the at least one cell containing heat exchange material and having a separate cooling element associated therewith corresponds to an area where deep immersion of tissue into the cushioning surface is expected to occur. Here, each separate cooling element may preferably comprise a powered thermoelectric cooler.

BRIEF DESCRIPTION OF THE DRAWINGS

The present disclosure is illustrated by way of example and not limitation in the figures of the accompanying drawings, in which.

DETAILED DESCRIPTION OF PREFERRED EMBODIMENTS

The following description, taken in conjunction with the referenced drawings, is presented to enable one of ordinary skill in the art to make and use the disclosure and to incorporate it in the context of particular applications. Various modifications, as well as a variety of uses in different applications, will be readily apparent to those skilled in the art, and the general principles, defined herein, may be applied to a wide range of aspects. The present disclosure is not intended to be limited to the aspects disclosed herein. Instead, it is to be afforded the widest scope consistent with the disclosed aspects.

According to a preferred embodiment of the present disclosure, cushioning surface 20 is actively and selectively cooled while also providing adequate cushioning effect for pressure redistribution Immersion is defined as the depth of penetration into a support surface (National Pressure Ulcer Advisory Panel 2006); distributing excess pressure to surrounding areas through immersion remains the fundamental strategy to reduce pressure near bony prominences (Brienza, et al. 2008). Lower density materials such as foam and constructs such as air chambers do not have the capacity to transfer heat away from the skin effectively. Denser materials with better heat transfer characteristics generally do not allow adequate immersion and envelopment for effective pressure redistribution.

Figure 1:
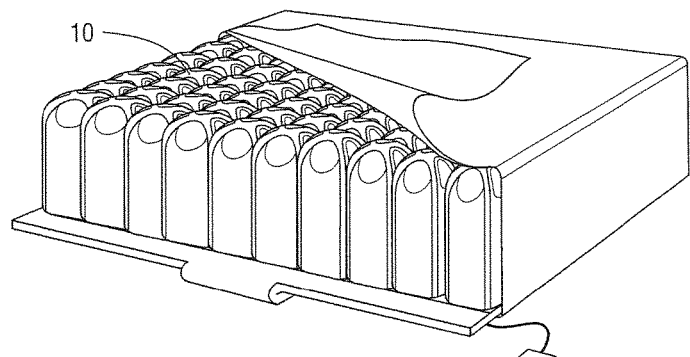
FIG. 1 shows an example of a typical, known segmented air, pressure reducing cushion.
Figure 2:
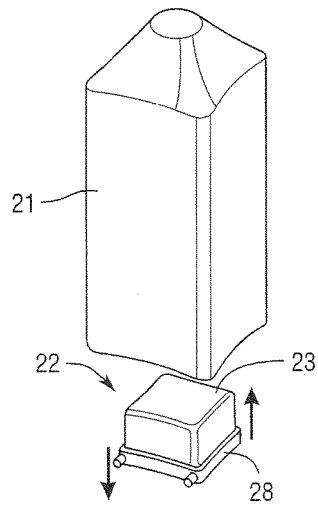
FIG. 2 shows an exploded view of an individually cooled cell of an actively and selectively cooled cushioning surface according to a preferred embodiment of the present disclosure.
Figure 3:
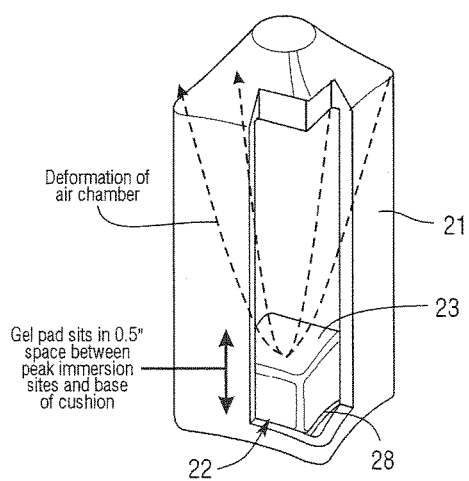
FIG. 3 shows a cut-away view of an individually cooled cell of an actively and selectively cooled cushioning surface according to a preferred embodiment of the present disclosure.

Prior studies have shown that pressure reducing cushions (PRCs) protect tissue integrity better than standard foam cushions (Geyer, et al. 2001). Pressure reducing cushions preferably can be constructed from a variety of materials including: viscoelastic foams, gels, water or other fluids, and segmented air cells (Sprigle, Press and Davis 2001). Multi-cell air cushions have been shown to provide superior pressure redistribution and are among the most effective types of wheelchair cushions. Typical, segmented air cell cushions 10 known in the art, such as the ROHO Cushion shown in FIG. 1, use a system of air cells that are made of neoprene rubber. Narrow channels that allow air to flow at a controlled rate from cell to cell interconnect the soft, flexible cells. A properly inflated segmented air cushion generally will allow a seated person to sink to within roughly 0.5 inches of clearance between the buttocks and the bottom of the cushion.

Preferred cushioning surfaces 20 of the present disclosure for cooling tissue that reaches a predefined level of immersion into cushioning surface 20 selectively cool deep immersed tissue without adversely affecting the pressure redistribution characteristics of the cushioning surface. According to preferred embodiments of the present disclosure, a preferred active and selectively cooled cushioning surface 20 contains one or more cooling elements 22, comprising a soft or compliant material with good heat exchange/conduction properties that are located deep within one or more individual cells or chambers 21 (see FIG. 4 for patterns 19 of individual cells 21A containing cooling elements 22 within cushioning surface 20 so that the cooling elements 22 only come in contact with tissue or body parts protruding deep into the cushioning surface 20). By introducing cooling elements 22 into the clearance space between the deeply immersed parts of the body and the bottom of the cushioning surface 20, zones of deepest immersion that correspond to areas of greatest risk of developing pressure ulcers are targeted for cooling.

Preferably, electrically powered thermoelectric coolers (TECs) 28 form a part of cooling elements 22 and are used to draw heat from pads 23 of compliant heat exchange material disposed in the targeted areas under the bony prominences of a supported or seated individual. The TECs 28 work by transferring heat from one side of the device to the other side against a temperature gradient (from cold to hot). Using several TECs 28 within or associated with the cushioning surface 20 will allow select areas of highest immersion beneath a seated or otherwise supported individual to be selectively cooled without inducing a systemic hypothermic response throughout the person's body.

As shown in drawings, particularly, FIGS. 2-7, preferably, gel pads or blocks 23 of compliant heat exchange material serve as the component of cooling elements 22 disposed between the TECs 28 and the seated or supported individual. There are two primary benefits to this approach; first that a soft, contouring gel pad 23 would have better contact with the skin and allow the cooling to be delivered more effectively. Second, the cushioning effect of the gel pad 23 can protect the user from the force applied when the user sits upon or is otherwise supported by cushioning surface 20 at the location of the TECs 28, where at the areas of deep immersion, the tissue or body part is likely to encounter components of the cooling elements 22 rather than the cushion of air in the clearance space of individual cells 21.

As shown in FIGS. 4-16, the hot side 28A of the TEC 28 (cool side of the TEC 28 is 28B) will be attached to or associated with a heat sink 30 to draw the generated heat away from the TEC 28 and gel pad 23. As the air cells 21 deform, the buttocks would come in contact with the gel pad 23, which is cooled by the TEC 28 situated at the base of cell 21A of cushioning surface 20.

Figure 4:
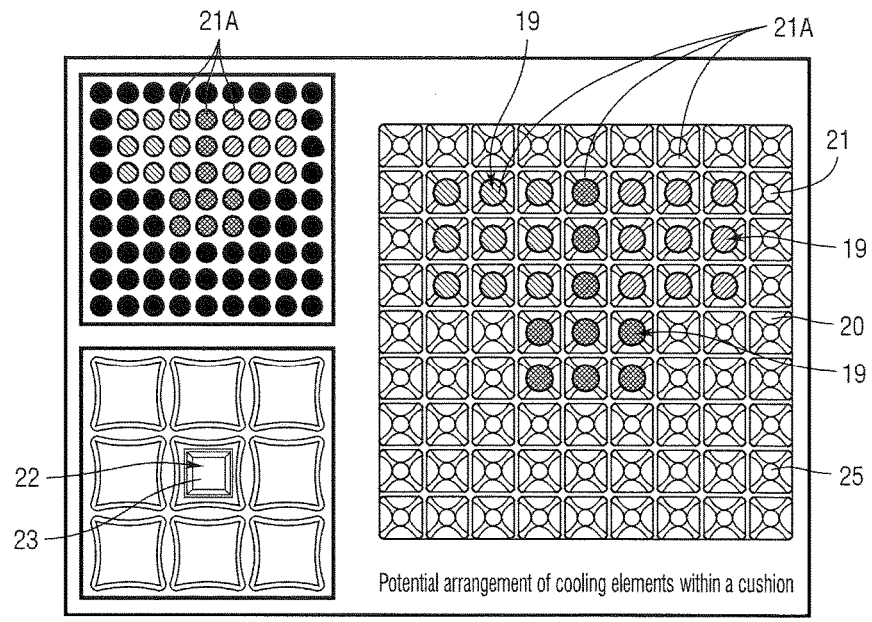
FIG. 4 shows several preferred patterns of individually cooled cells in an actively and selectively cooled cushioning surface according to preferred embodiments of the present disclosure.

Preferably, cooling elements 22 are arranged in arrays throughout cushioning surface 20 depending on the needs of the user. As shown in FIG. 4, different zones 19 beneath a user can be individually controlled and calibrated to cover small or large areas of targeted cooling through placement of cells 21A having cooling elements 22 disposed therein or associated therewith. Alternately, the cooling elements 22 might be activated when contact between the roof of the air chamber 21 and the gel block 23 is detected. Preferably, cooling properties (targeted temperature, cooling rate, etc.) will be determined based upon examining the effects of cooling.

Materials suitable for use as the gel pad 23 interface between the TECs 28 and a user seated or supported on the top 25 of cushioning surface 20 preferably need to be soft enough to produce relatively low reaction to increases in pressure when a user is in contact therewith, and thermally conductive enough to be cooled by the TEC 28 below while accepting the heat at the body surface interface. Conventional gel materials coupled with thermally conductive additives preferably allow gel pads 23 to combine requisite properties into one gel pad 23. Additional modifications could preferably be made to the housing material of each air cell 21, either through additives or modifications of thicknesses, which could further enhance the cooling effectiveness of TECs 28. In addition, other compliant materials such as phase change materials, like those disclosed in U.S. Pat. No. 6,699,266 (incorporated herein by reference), maybe used as the heat absorbing compliant element 23 embedded in individual cells 21A of cushioning surface 20.

Cushioning surface 20 preferably comprises a segmented air cell cushion 10, such as a single chamber high profile air cushion (ROHO Group, Belleville, Ill.) classified by CMS as an adjustable, skin protection cushion which provides suitable redistribution of pressure and shear. The overall construction of individual cells 21 allows for site-specific additions of interface cooling elements 22. Segmented air cell cushions 10, such as the ROHO brand shown in FIG. 1, use a system of cells 21 interconnected by channels that allow air to flow at a controlled rate from cell to cell. As this occurs, the bony prominences are immersed and enveloped in the cushion material, increasing the contact area and distributing the applied force on the buttocks or other supported body part. Thus, the cushioning surfaces 20 of the present disclosure may be used in wheelchair seating/support applications and other applications including, without limitation, beds, mattresses, mattress overlays, operating table pads, face masks, helmets and shoe insoles. A properly inflated segmented air cushion 10 will allow a seated person to sink to roughly 0.5" of clearance between the buttocks and the bottom of the cushioning surface 22; the internal pressure of the cushioning surface 20 supports the applied load of a seated/supported person. Preferably, a heat exchange material pad 23 is disposed into such clearance space of select cells 21 and cooled by a TEC 28 and an air-cooled heat sink 30, as shown in FIGS. 2, 3, 5, 5A, 6 and 7.

In another preferred embodiment, heat sink 30 is water-cooled or liquid-cooled and also located external to cushioning surface 20 and allows for placement of a majority of the waste heat removal components to a position underneath or behind the seat of wheelchair 15 while leaving a slimmer cooling plate component of heat sink 30 immediately below cushioning surface 20. Heat sink 30 in this water-cooled or liquid-cooled embodiment preferably comprises a ½ inch thick cold plate 3.5 inches wide and 12 inches long, which provides a surface area that will encompass all required TECs 28 corresponding with individually cooled cells 21A in cushioning surface 20. Preferably, copper tubing is embedded within the aluminum cold plate allowing liquid/water to be pumped through it to remove the waste heat from the TECs 28. Flexible tubing preferably connects to the ends of this copper tubing allowing the water to be directed from the cold plate to a passive radiator system located behind/below the seat of wheelchair 15 to dissipate the heat.

Figure 5:
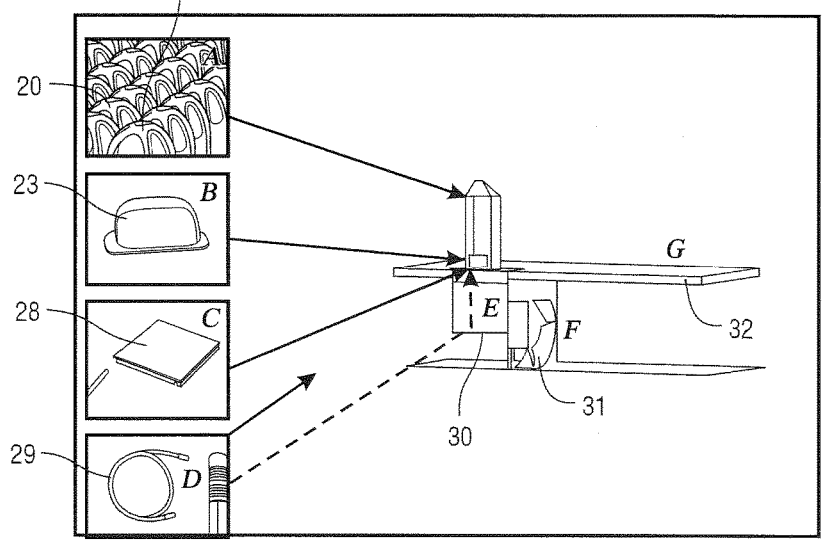
FIG. 5 shows a cut-away view of an individually cooled cell with an associated heat sink and fan of an actively and selectively cooled cushioning surface according to a preferred embodiment of the present disclosure.
Figure 5A:
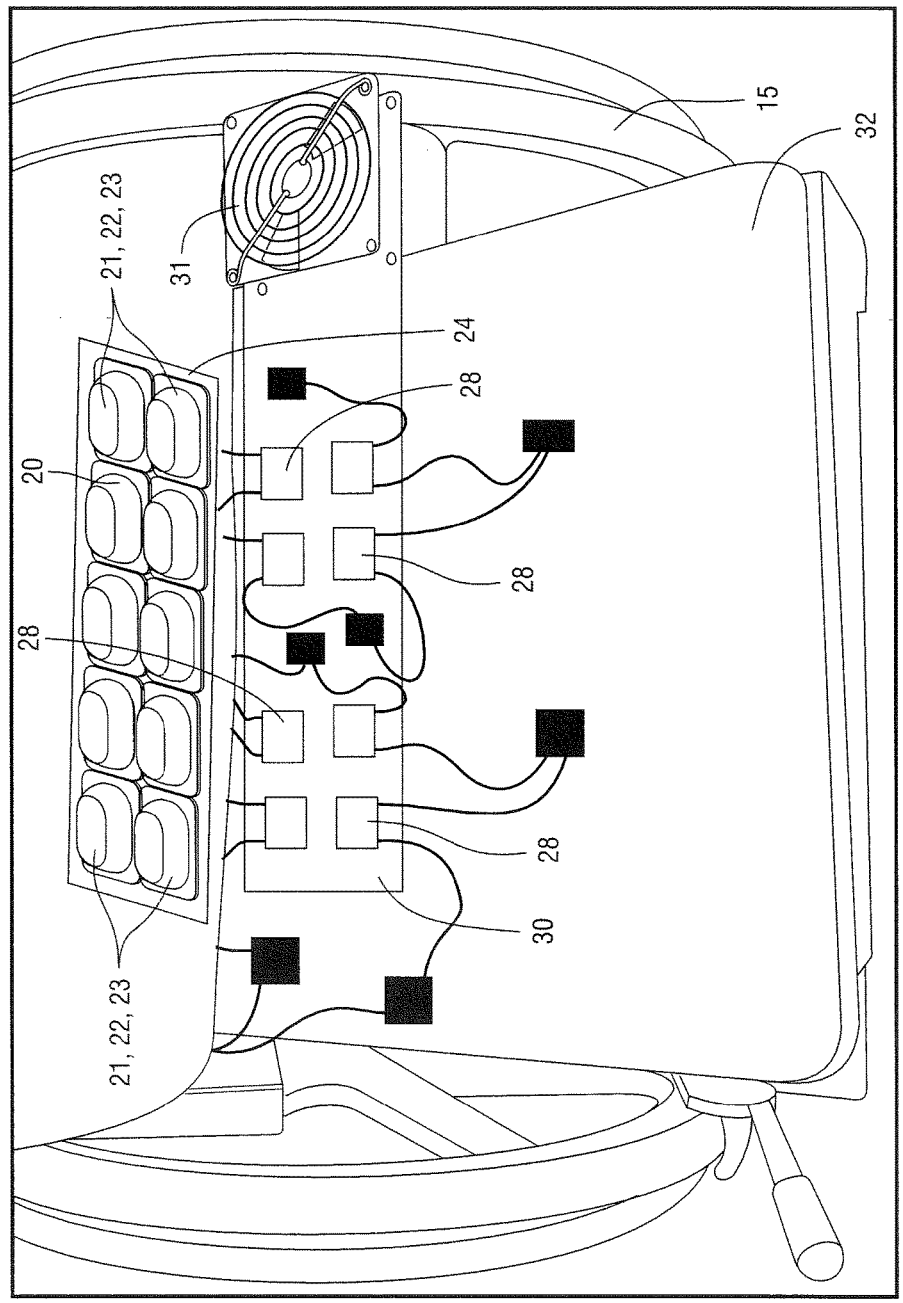
FIG. 5A shows a preferred embodiment of a wheelchair having a seat comprising an actively and selectively cooled cushioning surface according to a preferred embodiment of the present disclosure.

As shown particularly in FIG. 5, pads 23 of individual cooling elements 22 preferably are inserted through the base 24 of cushioning surface 20 into the individual air chambers 21. The gel pad 23 preferably is positioned atop a TEC 28 and the chamber 21 resealed around the TEC 28 using neoprene epoxy to maintain the internal pressure of the cushioning surface 20 used to support the user or load. The hot side 28A of the TEC 28 is fixed to or associated with heat sink 30 to draw the generated heat away from the TEC 28 and gel pad 23. As the air cells 21 deform, the buttocks or other body part depending upon the application of the cushioning surface 20 would come in contact with the gel pad 23, which is cooled by the TEC 28 situated, disposed in or otherwise associated with base 24 of cushioning surface 20. Preferably, individual cells 21A having cooling elements 22 associated therewith are arranged in arrays 19 throughout the cushioning surface 20 depending on the needs of the user, as shown in FIG. 4. Different patterns/zones 19 beneath a user could be individually controlled and calibrated to cover small or large areas of targeted cooling.

Figure 6:
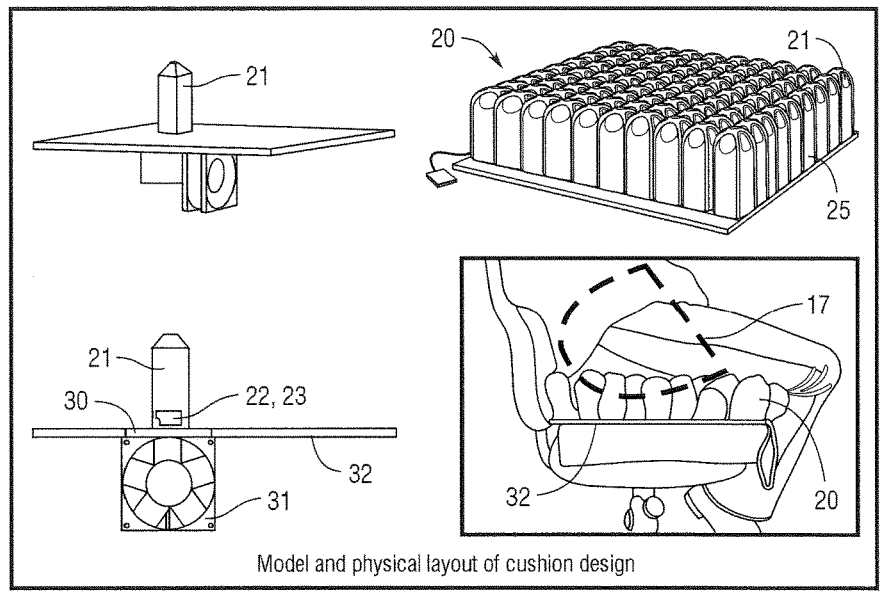
FIG. 6 shows various views and placements of an actively and selectively cooled cushioning surface and components thereof according to a preferred embodiment of the present disclosure.
Figure 7:
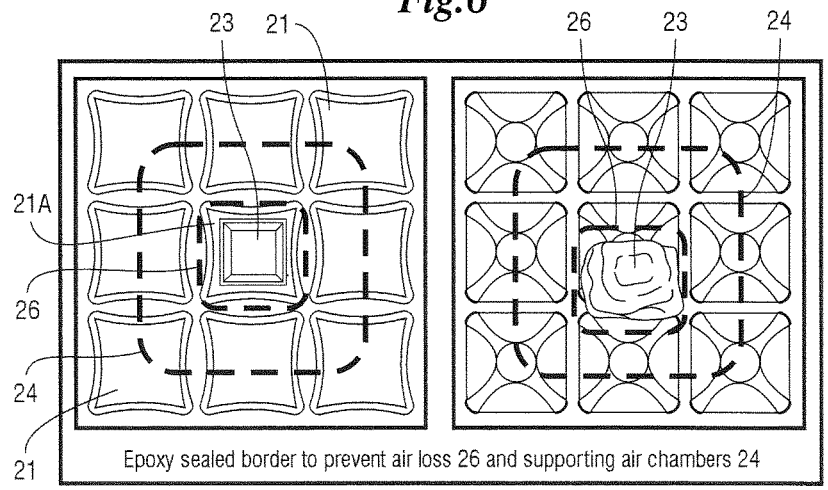
FIG. 7 shows placement and construction of an individually cooled cell of an actively and selectively cooled cushioning surface according to a preferred embodiment of the present disclosure.
Figure 8:
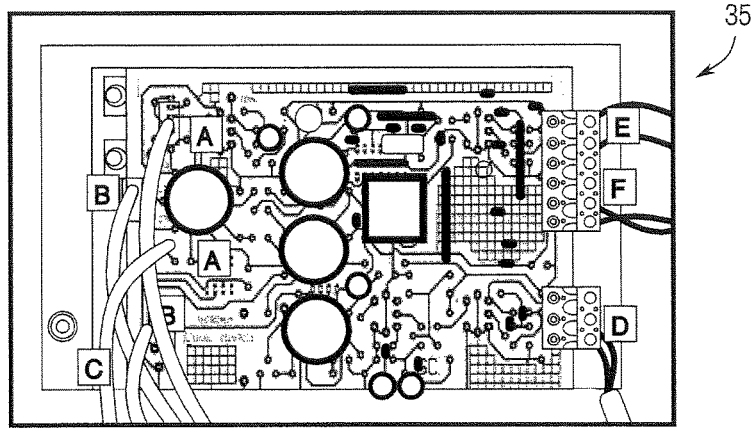
FIG. 8 shows a controller for use with an actively and selectively cooled cushioning surface according to a preferred embodiment of the present disclosure.

A preferred cushioning surface 20 was fabricated according to the present disclosure as shown particularly in FIGS. 2-7 and 11-16 and comprises a single chamber, high profile ROHO cushion 10 (model: 1R99C) disposed upon support frame 32 whose height accommodated the heat sink 30 and cooling fan 31. The heat sink 30 preferably was machined from aluminum to a 76.2×63.5×63.5 mm block (3)(2.5)(2.5 in.) and has a basic fin design (spaced 2 mm apart) to allow convection to dissipate the heat created by TECs 28. Aluminum 6061 was used due to its thermal properties and ease of machining (specific heat A1 6061: 0.896 J/g-° C., thermal conductivity: 167 W/m-K). A Hengshan (Hengshan Group, FS70252M, Taiwan). CPU cooling fan 31 was oriented perpendicular to the fins with the design of increasing convection to ambient air. Gel pad 23 was set into the base of cushioning surface 20 located where the left ischial tuberosity (IT) was expected to be immersed into the cushioning surface 20. FIG. 6 shows several views of this preferred design with the dashed line 17 around buttocks of a seated person illustrates the alignment of the seated user on cushioning surface 20.

Preferred gel or heat exchange pads 23 for use in the cushioning surface 20 of the present disclosure comprise glycerin hydrogels bound in urethane film and press fit into the base of a cell 21 of cushioning surface 20. Each gel pad 23 of this design is designed to cool approximately 645.16 $mm^2$ (1 $in^2$) while in contact with the buttocks or other deep immersed tissue.

The interface between the gel pad 23 and TEC 28 preferably is coated in a thin layer of thermal grease 27 (Thermal Joint Compound, Wakefield Thermal Solutions, Pelham N.H.) to increase heat conduction. The border 26 surrounding the bottom 24 of severed air chamber 21 preferably is sealed with airtight thermal epoxy (Royal Adhesives & Sealants, LLC, Belleville N.J.). This prevents any appreciable loss of air pressure from within cushioning surface 20.

Figure 9:
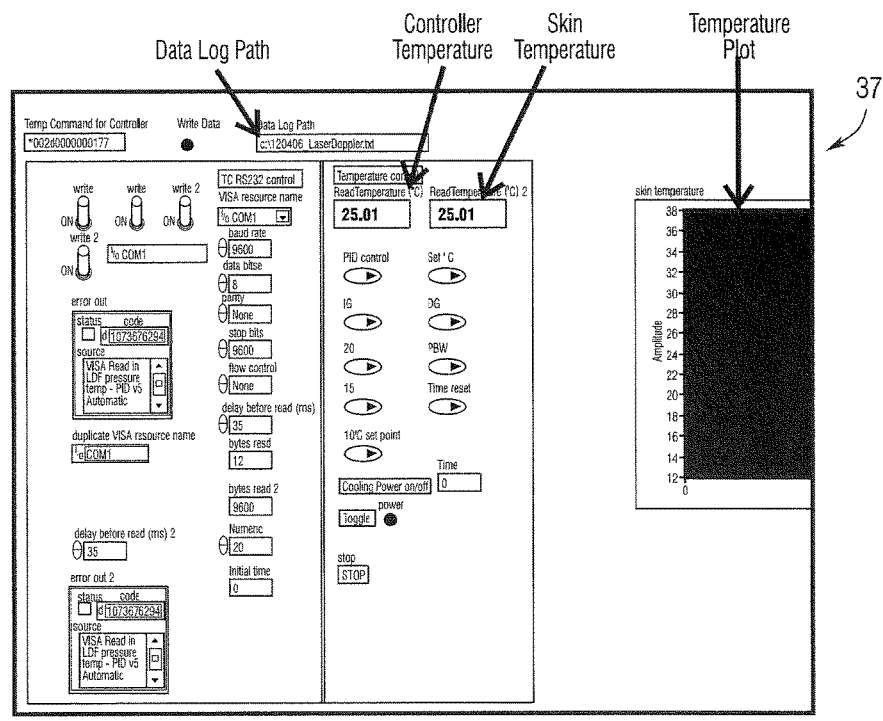
FIG. 9 shows a GUI of a software program for use with an actively and selectively cooled cushioning surface according to a preferred embodiment of the present disclosure.
Figure 10:
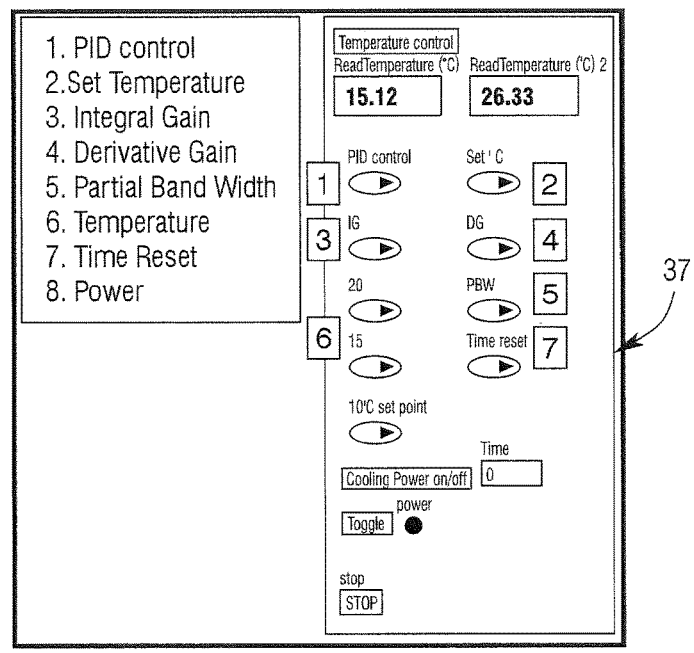
FIG. 10 shows another GUI of a software program for use with an actively and selectively cooled cushioning surface according to a preferred embodiment of the present disclosure.

Preferred closed-loop TECs 28 (TE Technology, Traverse City, Mich.) are used to keep skin interface temperature at approximately 25° C. TEC 28 (TE-71-1.0-1.3) and heat sink preferably may be attached using a press fit and thermal grease. Two thermistors 29 (MP-2444) preferably were placed in the system to monitor interface temperature and send feedback to the temperature control board 35 (FIG. 8) (TC-36-25-RS232). The feedback control thermistor 29 preferably may be imbedded within the gel pad 23, and the interface thermistor 29 preferably may be placed between the seated participant and top of cushioning surface 20. The control board 35 is a device that controls the voltage and the current that is delivered to the TEC 28 by receiving commands from an associated computer. The controller 35 preferably utilizes a proportional-integral-derivative (PID) control scheme to maintain the temperature of the TEC 28. As shown in FIGS. 9-10, the board 35 preferably may be controlled from a Labview program 37 (Version 8.6, National Instrument, Austin, Tex.) which transmitted all parameters of the controller program. The program 37 preferably is capable of recording temperature vs. time data in ASCII files and displayed the controller and interface temperatures in real time.

Figure 11:
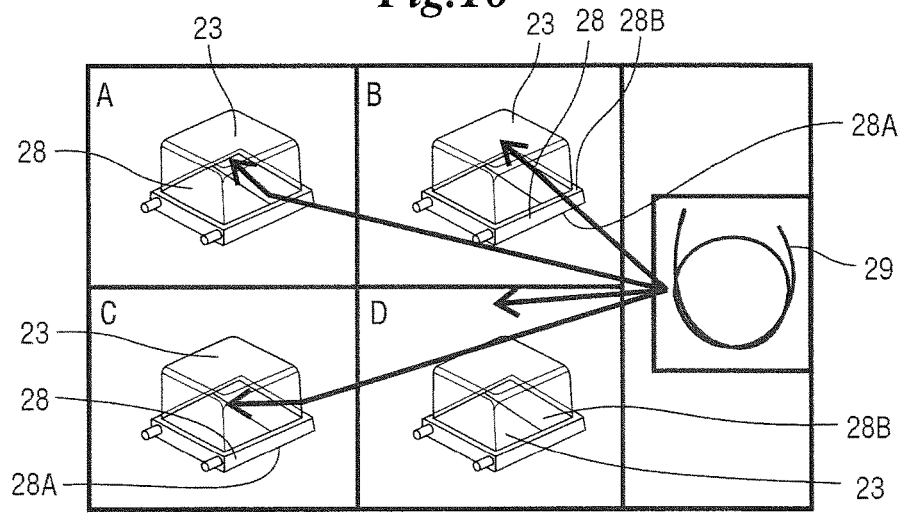
FIG. 11 shows preferred placements for control thermistors used with an actively and selectively cooled cushioning surface according to preferred embodiments of the present disclosure.

Optimal use of the PID controller 35 depended upon the location of the sensing thermistor 29 that would give feedback to the system for the closed loop control. As shown in FIG. 11, preferred locations of the sensing thermistor 29 included within the supporting gel pad 23, atop the supporting gel pad 23, below the gel pad 23 directly in contact with TEC 28, and outside the cooling element 22 on the skin of the seated individual. To evaluate the effect of location of thermistor 29 and set point on interface temperature delivery, an experiment was conducted using a preferred hydrogel gel pad 23. The goal was to determine which preferred setups would approach 25±1° C. The highest temperature set point possible was preferred, since the TEC 28 requires proportionally more power and generates more heat as the target temperature decreases. The conditions tested were 20, 15, and 10° C. temperature set points. The locations of control thermistor 29 investigated included within the gel pad 23, atop the gel pad 23, and between the gel pad 23 and TEC 28. Thermistor control at the skin was not evaluated as it was deemed impractical for standard everyday use of a functional cushioning surface 20. The most successful trials were 15 or 10° C. set points with the control thermistor 29 placed within the gel pad 23 or on top of gel pad 23. Set point and location combinations with the lowest power requirements and generated heat are preferred. A set point of 15° C. combined with the control thermistor within the gel pad 23 effectively produced an interface temperature of 25°±1° C. (max stdev=0.85° C. during steady state). The TEC 28 temperature also oscillated at 15±0.2° C., which demonstrated the control board 35 was operating within its appropriate bandwidth.

Figure 12:
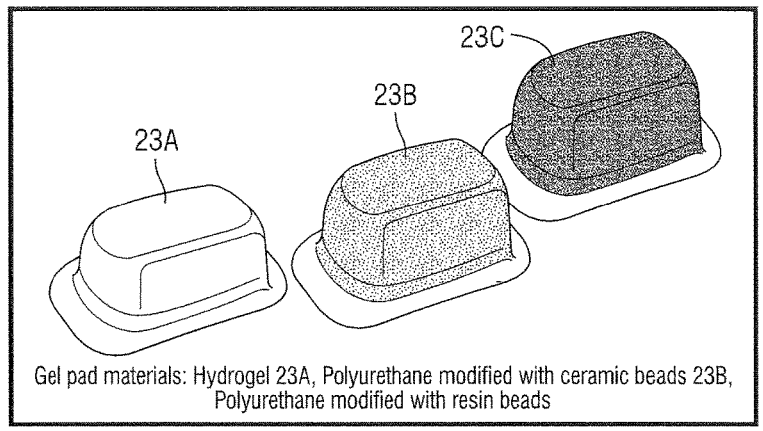
FIG. 12 shows preferred heat exchange materials in pad form for use in an actively and selectively cooled cushioning surfaces according to preferred embodiments of the present disclosure.
Figure 13:
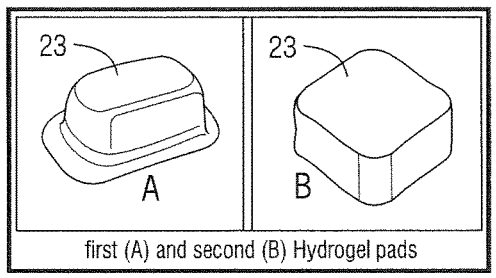
FIG. 13 shows preferred heat exchange materials in pad form for use in an actively and selectively cooled cushioning surfaces according to preferred embodiments of the present disclosure.
Figure 14:
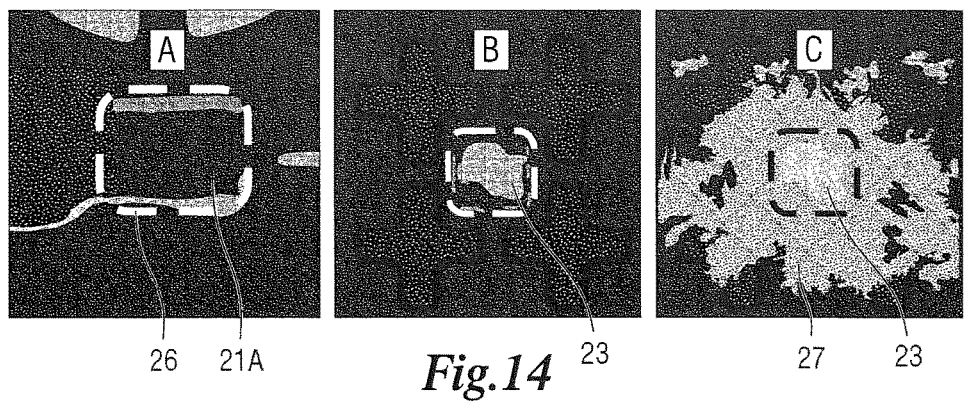
FIG. 14 shows placement and construction of an individually cooled cell of an actively and selectively cooled cushioning surface according to a preferred embodiment of the present disclosure.

As shown in FIG. 12, preferred heat exchange materials for gel pads 23 include (i) a glycerin hydrogel 23A bound in urethane film, (ii) a polyurethane gel 23B modified with ceramic microspheres and (iii) a polyurethane gel 23C with resin microspheres. Each material was designed to maximize thermal conductivity while still providing adequate cushion support at the interface with the buttocks or other supported body part. According to another preferred embodiment of the present disclosure, the size of the gel pads 23 was increased slightly, as shown in FIG. 13, in an attempt to minimize effects of weight shifts or leaning by the user causing gel pad 23 to lose contact with an associated TEC 28. Preferably, by increasing the height and width of gel pad 23, more continuous contact between gel pad 23 and TEC 28 would be maintained with a user seated on or supported by cushioning surface 20. Moreover, the polyurethane membrane binding the gel pad 23 was removed according to this preferred embodiment to increase thermal transfer between the TEC 28, gel pad 23, and application site 19. Preferably, the larger gel pads 23 fully occupy a cell 21 of cushioning surface 20 but provide enough clearance to allow air redistribution between neighboring cells 21. As shown in FIG. 14, in this preferred embodiment only material from the underside 24 of cushioning surface 20 was removed leaving a void (FIG. 14A) which is then filled with a larger gel pad 23, which is held in place by compressive forces and secured using Neo-rez neoprene epoxy (Wahoo International Inc., Oceanside Calif.) (FIG. 14B). After curing, the control thermistor 29 preferably is punctured into the body of gel pad 23, and a small amount of epoxy is used to secure it in place. Finally, this cooling element 22 is covered in thermal grease 27 (FIG. 14C) to facilitate heat transfer to a TEC 28 unit aligned below it (see FIGS. 2-3, 5, 5A, 6 and 11).

Figures 15A, 15B:
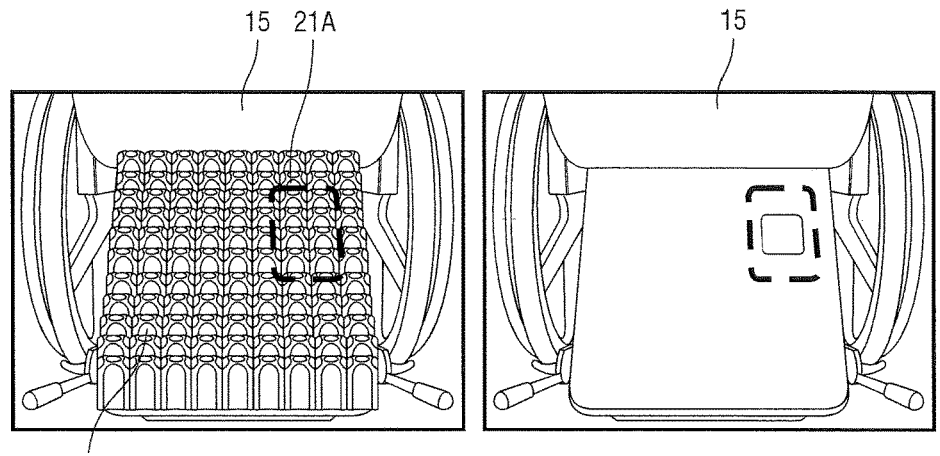
FIG. 15A shows a preferred embodiment of a wheelchair having a seat comprising an actively and selectively cooled cushioning surface according to a preferred embodiment of the present disclosure.
FIG. 15B shows another view without seat cushion of the wheelchair of FIG. 15A as modified for use with an actively and selectively cooled cushioning surface according to a preferred embodiment of the present disclosure.
Figure 16:
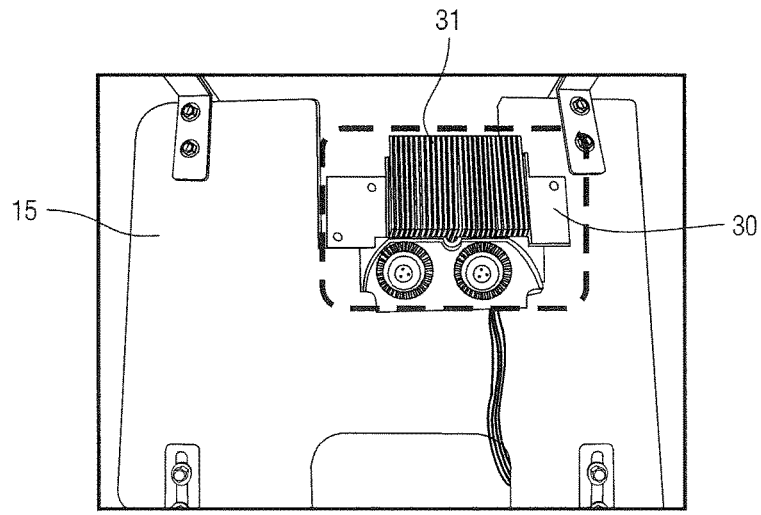
FIG. 16 shows a bottom view of a seat of a wheelchair modified for use with an actively and selectively cooled cushioning surface according to a preferred embodiment of the present disclosure.

FIGS. 15-16 illustrate a preferred embodiment of a wheelchair 15 having a seat comprising a cushioning surface 20 of the present disclosure. In this embodiment, support base 32 of cushioning surface 20 was modified to fit a 16"×17" Quickie (Breezy Ultra 4) wheelchair frame. A drop seat platform was machined to accommodate the aluminum heat sink 30 below a seated user. A cooling fan 31 from Delta Products (SFB0212HH-F00, Fremont Calif.) is preferably aligned perpendicular to the orientation of the fins to increase convective heat transfer. Fan 31 offered a wider cooling area with dual rotors and dimensions that matched those of the heat sink 30. The fan 31 and heat sink 30 were aligned to where cell 21A (containing cooling element 22 comprising heat exchange pad 23 and TEC 28) would be located to align with an IT to be cooled in normal seating position.

It should be understood that while this disclosure has been described herein in terms of specific, preferred embodiments set forth in detail, such embodiments are presented by way of illustration of the general principles of the disclosure, and the disclosure is not necessarily limited thereto. Certain modifications and variations in any given material, process step or chemical formula will be readily apparent to those skilled in the art without departing from the true spirit and scope of the present disclosure, and all such modifications and variations should be considered within the scope of the claims that follow.

What is claimed is:

1. A cushioning surface for cooling a body part or tissue immersed into the cushioning surface, comprising:
    a segmented fluid cushion comprising a plurality of cells interconnected to allow fluid to flow from each cell to at least one of the other plurality of cells;
    wherein each of the cells comprises first and second opposing sides and one or more sidewalls which collectively define a chamber in which part of the fluid is disposed;
    wherein one or more of the plurality of cells contains heat exchange material disposed in a clearance space within the chamber in each such cell near the second side of the cell;
    a cooling element associated with and for removing heat from the one or more cells containing the heat exchange material, wherein the heat exchange material in each of the one or more cells is disposed on or very near the cooling element; and
    wherein the heat exchange material in each of the one or more cells is disposed between the first and second sides so that only a body part or tissue reaching a level of immersion into the cushioning surface from the first side to the second side and into or near the clearance space of the one or more cells containing heat exchange material is cooled by such cells and the cooling element.

2. The cushioning surface of claim 1 wherein the fluid is air.

3. The cushioning surface of claim 1 wherein the cooling element comprises a powered thermoelectric cooler.

4. A cushioning surface for cooling a body part or tissue immersed into the cushioning surface, comprising:
    a segmented fluid cushion comprising a plurality of cells interconnected to allow fluid to flow from each cell to at least one of the other plurality of cells;
    wherein each of the cells comprises first and second opposing sides and one or more sidewalls which collectively define a chamber in which part of the fluid is disposed;
    wherein one or more of the plurality of cells contains a heat exchange material disposed in a clearance space within the chamber in each such cell near the second side of the cell;
    a separate cooling element associated with each of the one or more cells containing the heat exchange material; wherein the heat exchange material in each of the one or more cells is disposed on or very near its separate cooling element; and
    wherein the heat exchange material in each of the one or more cells is disposed between the first and second sides so that only a body part or tissue reaching a level of immersion into the cushioning surface from the first side to the second side and into or near the clearance space of the one or more cells containing heat exchange material is cooled by such cells and their respective cooling elements.

5. The cushioning surface of claim 4 wherein each cooling element comprises a powered thermoelectric cooler.

6. The cushioning surface of claim 4 wherein each of the one or more cells containing the heat exchange material and having the separate cooling element associated therewith corresponds to an area where immersion of a body part or tissue, from a body supported by the cushioning surface, extends into or near the clearance space of the one or more cells containing heat exchange material.

7. The cushioning surface of claim 4 wherein each of the one or more cells containing the heat exchange material and having the separate cooling element associated therewith corresponds to an area where immersion of a body part or tissue, from a person seated on the cushioning surface, extends into or near the clearance space of the one or more cells containing heat exchange material.

8. A cushioning surface for cooling a body part or tissue immersed into the cushioning surface, comprising:
- a segmented fluid cushion comprising a plurality of cells interconnected to allow fluid to flow from each cell to at least one other of the plurality of cells;
- wherein each of the cells comprises first and second opposing sides and one or more sidewalls which collectively define a chamber in which part of the fluid is disposed;
- wherein a plurality of the plurality of cells contains a heat exchange material disposed in a clearance space within the chamber space in each such cell near the second side of the cell;
- a separate cooling element associated with each of the cells containing heat exchange material, wherein the heat exchange material in each of the cells is disposed on or very near its separate cooling element; and
- wherein the heat exchange material in each of the plurality of the plurality of cells is disposed between the first and second sides so that only a body part or tissue reaching a level of immersion into the cushioning surface from the first side to the second side and into or near the clearance space of the one or more of the cells containing heat exchange material is cooled by such cells and their respective cooling elements.

9. The cushioning surface of claim 8 wherein each cell containing the heat exchange material and having the separate cooling element associated therewith corresponds to an area where immersion of a body part or tissue extends into or near the clearance space of the one or more of the cells containing heat exchange material from a body supported by the cushioning surface.

10. The cushioning surface of claim 8 wherein each cell containing the heat exchange material and having the separate cooling element associated therewith corresponds to an area where immersion of a body part or tissue extends into or near the clearance space of the one or more of the cells containing heat exchange material from a person seated on the cushioning surface.

11. The cushioning surface of claim 8 wherein each of the separate cooling elements comprises a powered thermoelectric cooler.

12. A cushioning surface for cooling a body part or tissue immersed into the cushioning surface, comprising:
- a segmented air cushion comprising a plurality of cells interconnected to allow air to flow from each cell to at least one other of the plurality of cells;
- wherein each of the cells comprises first and second opposing sides and one or more sidewalls which collectively define a chamber in which part of the air is disposed;
- wherein one of the plurality of cells contains a heat exchange material disposed in a clearance space within the chamber in the one cell near the second side of the cell;
- a cooling element associated with the one cell containing the heat exchange material wherein the heat exchange material in the one cell is disposed on or very near the cooling element; and
- wherein the heat exchange material in the one cell is disposed between the first and second sides so that only a body part or tissue reaching a level of immersion into the cushioning surface from the first side to the second side and into or near the clearance space of the one cell containing heat exchange material is cooled by the cushioning surface.

* * * * *